(12) United States Patent
Kiesele et al.

(10) Patent No.: US 8,187,437 B2
(45) Date of Patent: May 29, 2012

(54) ELECTROCHEMICAL GAS SENSOR

(75) Inventors: Herbert Kiesele, Lübeck (DE); Frank Mett, Lübeck (DE); Sabrina Sommer, Lübeck (DE)

(73) Assignee: Dräger Safety AG & Co. KGaA, Lübeck (DE)

( * ) Notice: Subject to any disclaimer, the term of this patent is extended or adjusted under 35 U.S.C. 154(b) by 431 days.

(21) Appl. No.: 12/475,826

(22) Filed: Jun. 1, 2009

(65) Prior Publication Data
US 2010/0012494 A1    Jan. 21, 2010

(30) Foreign Application Priority Data
Jul. 19, 2008  (DE) .................. 10 2008 033 828

(51) Int. Cl.
*G01N 27/26* (2006.01)
*G01N 17/00* (2006.01)
*G01F 1/64* (2006.01)

(52) U.S. Cl. .............. 204/431; 204/432; 205/786.5

(58) Field of Classification Search ............. 204/431, 204/432; 205/786.5
See application file for complete search history.

(56) References Cited

U.S. PATENT DOCUMENTS

| | | | |
|---|---|---|---|
| 6,584,827 B2 | 7/2003 | Kiesele et al. | |
| 6,607,642 B1 | 8/2003 | Kiesele et al. | |
| 2005/0245784 A1* | 11/2005 | Carson et al. | 588/302 |
| 2007/0227909 A1 | 10/2007 | Sommer et al. | |
| 2007/0227910 A1 | 10/2007 | Sommer et al. | |
| 2008/0035493 A1* | 2/2008 | Sommer et al. | 205/786.5 |

FOREIGN PATENT DOCUMENTS

| | | |
|---|---|---|
| DE | 19939011 | 1/2001 |
| DE | 10144862 | 3/2003 |
| DE | 102004062051 A1 | 7/2006 |
| DE | 102006014714 B3 | 5/2007 |
| DE | 102006014715 B3 | 6/2007 |
| DE | 102006014713 | 11/2007 |
| GB | 2317704 A | 4/1998 |
| GB | 2353363 A | 2/2001 |
| GB | 2436695 A | 10/2007 |
| GB | 2436696 A | 10/2007 |
| GB | 2437610 A | 10/2007 |
| WO | WO 2006047086 A1 * | 5/2006 |

OTHER PUBLICATIONS

Khudaish, E.A., A-Hinai, A.T. "The catalytic activity of vanadium pentoxide film modified electrode on the electrochemical oxidation of hydrogen sulfide in alkaline solutions." Journal of Electroanalytical Chemistry, vol. 587, pp. 108-114, Dec. 9, 2005.*

Jeroschewski, P., Steuckart, D., Kuhl, M. "An amperometric microsensor for the determination of H2S in Aquatic Environments" Analytical Chemistry, vol. 68, No. 24, pp. 4351-4357, Dec. 15, 1996.*

* cited by examiner

*Primary Examiner* — Jeffrey T Barton
*Assistant Examiner* — Louis Rufo
(74) *Attorney, Agent, or Firm* — McGlew and Tuttle, P.C.

(57) ABSTRACT

A mediator-based electrochemical gas sensor reacts selectively with hydrogen sulfide. The gas sensor has an electrolyte solution (9), which contains a mediator compound in the form of metallates of transition metals.

19 Claims, 3 Drawing Sheets

ELECTROCHEMICAL GAS SENSOR

CROSS REFERENCE TO RELATED APPLICATIONS

This application claims the benefit of priority under 35 U.S.C. §119 of German Patent Application DE 10 2008 033 828.1 filed Jul. 19, 2008, the entire contents of which are incorporated herein by reference.

FIELD OF THE INVENTION

The present invention pertains to an electrochemical gas sensor with a mediator compound.

BACKGROUND OF THE INVENTION

An electrochemical gas sensor with a mediator dissolved in the electrolyte is known from DE 10 2004 062 051 A1. The presence of a mediator offers the possibility of providing sensors that are highly selective for the analyte gas. The mode of operation of a gas sensor with a mediator is based on the fact that analyte gas diffuses through the measuring electrode into the electrolyte solution and is oxidized or reduced by the mediator. The analyte is converted in the process into a decomposition product and the mediator into an intermediate product, which is reoxidized or re-reduced at the measuring electrode. The electron transfer needed for this, which is proportional to the percentage of analyte gas in the gas sample, can be detected as the measured current.

Electrochemical gas sensors with mediators are characterized by a low residual current, high long-term stability and low cross sensitivity to interfering gases. Suitable mediators are available so far for special detection reactions only. However, the sensitivity of detection of the electrochemical gas sensor is also affected by the electrode material of the gas sensor.

An electrochemical gas sensor with a plurality of electrodes and a measuring electrode made of diamond-like carbon (DLC) is known from DE 199 39 011 B1. The measuring electrode is produced by means of a coating process, in which diamond-like carbon is applied to a gas-permeable membrane by means of a sputtering process. The measuring electrodes made of DLC have very high long-term stability.

An electrochemical gas sensor with a measuring electrode consisting of boron- or nitrogen-doped diamond (BDD) is known from DE 101 44 862 A1. The measuring electrode material is applied as a thin layer to a porous, gas-permeable substrate. Such measuring electrodes have a very high long-term stability and an extremely large potential window, so that very difficult-to-oxidize substances can be reacted as well.

An electrochemical measuring device, in which the measuring electrode has carbon nanotubes, is known from DE 10 2006 014 713 B3. This sensor contains a mediator based on a transition metal, it selectively detects $SO_2$ and avoids the formation of elemental sulfur, but has only a low sensitivity for $H_2S$.

SUMMARY OF THE INVENTION

A basic object of the present invention is to propose a mediator-based electrochemical gas sensor, which selectively detects hydrogen sulfide.

According to the invention, an electrochemical gas sensor is provided for detecting $H_2S$ in a gas sample. The electrochemical gas sensor comprises a measuring electrode, another electrode and an electrolyte solution containing a mediator compound in the form of metallates of transition metals.

The mediator system specified according to the present invention is based on the fact that the hydrogen sulfide is oxidized into sulfuric acid and the formation of elemental sulfur is thus avoided and high sensitivity is reached at the same time.

Mediators are preferably not fully soluble in an electrolyte solution. The use of suspensions or solutions of the mediator with solid undissolved solute offers a number of advantages, such as:

constant mediator concentration at variable atmospheric humidity,
identical equilibrium potentials at the measuring electrode and the auxiliary electrode if the measuring electrode and the auxiliary electrode consist of carbon,
filtering action of the solid undissolved solute, and
the sensor can be operated under anaerobic conditions if the measuring electrode and the auxiliary electrode consist of carbon and the mediator determines the potential of these electrodes.

Metallates of transition metals are used in the case of the mediator compound according to the present invention. The suitable metallates are vanadates, chromates, molybdates, tungstates, and permanganates. Molybdates of a transition metal salt are especially advantageous.

A 2 molar to 10 molar and preferably 3 molar aqueous lithium chloride solution, which covers a wide range of temperatures and humidities, is preferably used as the conductive electrolyte. It is also possible to use ammonium halides if organic solvents, for example, ethylene carbonate or propylene carbonate, are used. It is also possible to use ionic liquids, for example, substituted ammonium, phosphonium or imidazolium compounds.

The preparation of an aqueous electrolyte suspension will be described below.

As much copper chloride is added to an aqueous lithium chloride solution as is needed to obtain a concentration between 0.5 molar and 5.0 molar and preferably 3.0 molar. The following reagents are also added to the resulting chloro complexes:

Metallates: Chromates, vanadates, tungstates, but preferably molybdates. The concentration of the metallates is between 0.2 molar and 2 molar and preferably 1.0 molar,
inorganic acids or salts such as $NaHSO_4$. Both the residual current and the t90 time can be markedly reduced with these additives.

Polybasic carboxylic acids and their salts, preferably citric acid, phthalic acid as well as citrates and phthalates, are suitable for stabilizing the pH value. Boric acid or its salts may also be used as a polybasic acid.

The resulting concentration of the reagents should be 0.5 mol to 5.0 mol and preferably 1.0 mol per L. Besides the catalytic activity, these compounds also have pH-buffering properties, so that the gas can be admitted to the sensors over many hours without loss of sensitivity.

When the individual components are combined, a green solution is formed at first, from which a precipitate precipitates after some time. Hygroscopic alkali or alkaline earth metal halides, preferably chlorides, may also be used as conductive electrolytes in an aqueous solution. An especially preferred formula is 3.0 molar LiCi, 3.0 molar $CuCl_2$ and 1.0 molar $Li_2MoO_4$.

The measuring electrode preferably consists of diamond-like carbon. However, it is also possible to use other carbon materials, for example, carbon nanotubes or measuring electrodes made of boron- or nitrogen-doped diamond (BDD) or precious metal thin-layer electrodes.

Measuring electrodes made of carbon nanotubes (CNT) have long-term stability, can be integrated in existing sensor constructions in a simple manner, are suitable for many mediators, and can be purchased at a low cost. There are only a few cross sensitivities caused by the electrode material. This applies especially to multiwall carbon nanotubes (MW CNT). The carbon nanotubes are preferably used without binder. Such measuring electrodes are wetted by the electrolyte solution over their entire surface, as a result of which a large surface is obtained for the electrochemical reaction. The measuring electrode according to the present invention is preferably also permeable to gases. A measuring electrode made of CNT has better conductivity than a comparable measuring electrode made of DLC.

The layer thickness of the carbon nanotubes at a measuring electrode depends on the structure of the measuring electrode. If the carbon nanotubes are in the form of multiwall carbon nanotubes, the layer thickness is between one µm and a thousand µm, and preferably between 50 µm and 150 µm. The layer thickness is between 0.5 µm and 100 µm and preferably between 10 µm and 50 µm in case of single-wall carbon nanotubes.

The layer thickness also depends on the purity of the material. The layer thickness is closer to the lower end of the range in case of materials of an especially high purity.

A large-area contact is obtained between the material of the measuring electrode and the analyte or with the converted mediator due to the use of carbon nanotubes, so that complete oxidation or reduction takes place. Part of the analyte or of the reacted mediator is thus prevented from diffusing into the electrolyte space.

If the measuring electrode is designed as a precious metal thin-layer electrode, the layer thickness is less than 600 µm. Thick-layer electrodes have not proved to be successful because they have high residual currents and low selectivities.

The auxiliary electrode advantageously consists of a precious metal, for example, gold, platinum or iridium, and alternatively of carbon nanotubes.

A reference electrode or a protective electrode, which consists of a precious metal or carbon nanotubes, may also be present in addition to the auxiliary electrode.

An exemplary embodiment of the present invention is shown in the figures and will be explained below. The various features of novelty which characterize the invention are pointed out with particularity in the claims annexed to and forming a part of this disclosure. For a better understanding of the invention, its operating advantages and specific objects attained by its uses, reference is made to the accompanying drawings and descriptive matter in which preferred embodiments of the invention are illustrated.

DESCRIPTION OF THE PREFERRED EMBODIMENTS

Figure 1:
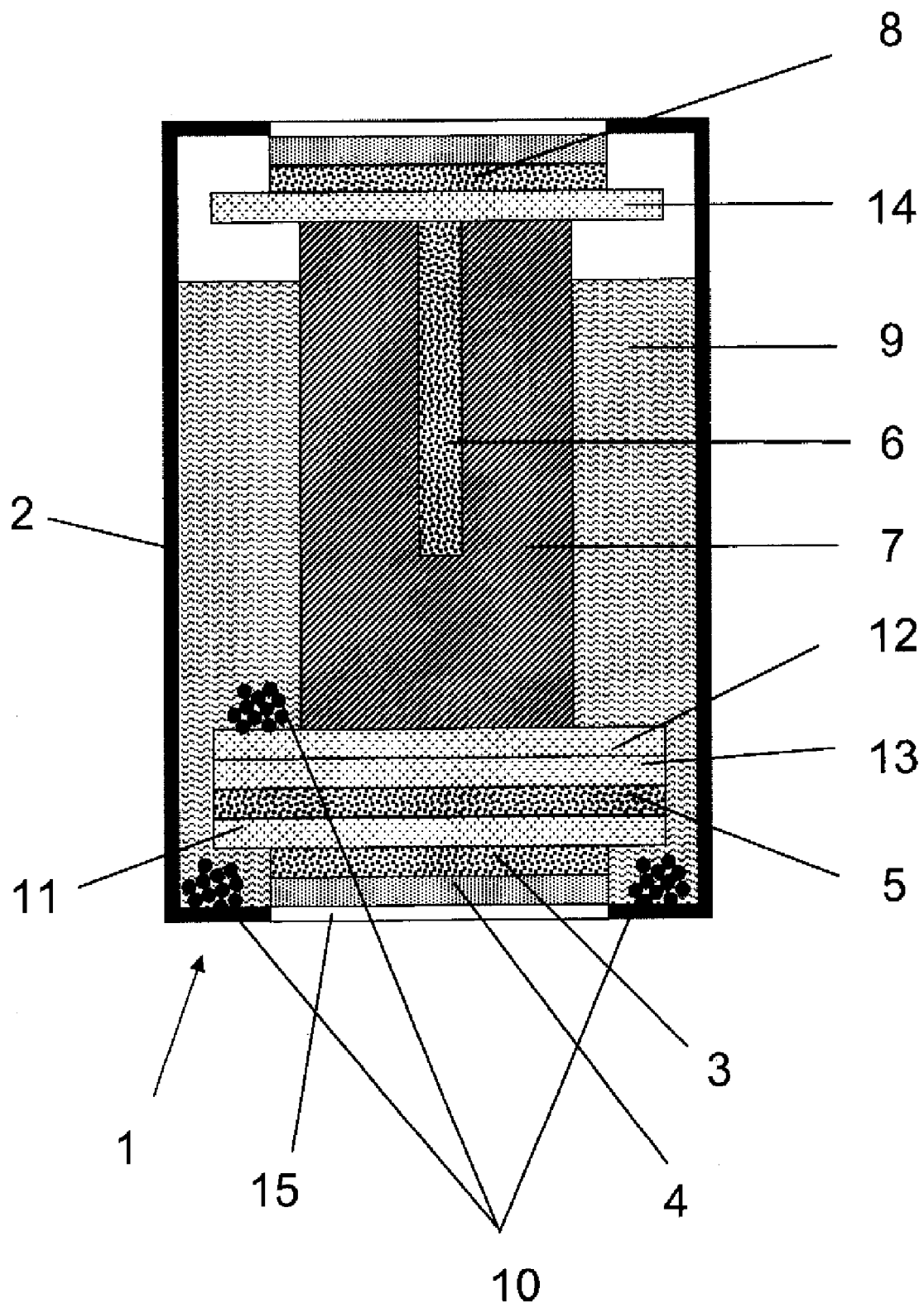
FIG. 1 is a sectional schematic view of an electrochemical gas sensor according to the invention.

Referring to the drawings in particular, a measuring electrode 3 made of diamond-like carbon (DLC) on a diffusion membrane 4, a protective electrode 5, a reference electrode 6 in a wick 7 and an auxiliary electrode 8 are arranged in a sensor housing 2 in the embodiment of the electrochemical sensor 1 illustrated in FIG. 1. The interior space of the sensor housing is filled with an electrolyte-mediator mixture 9, wherein the mediator is additionally also present as a solid undissolved solute 10. The electrodes 3, 5, 6, 8 are held at fixed distances from one another by means of liquid-permeable nonwoven mats 11, 12, 13, 14. The gas enters through an opening 15 in the sensor housing 2. The electrochemical sensor 1 is connected in the known manner to a potentiostat, not shown in more detail.

Figure 2:
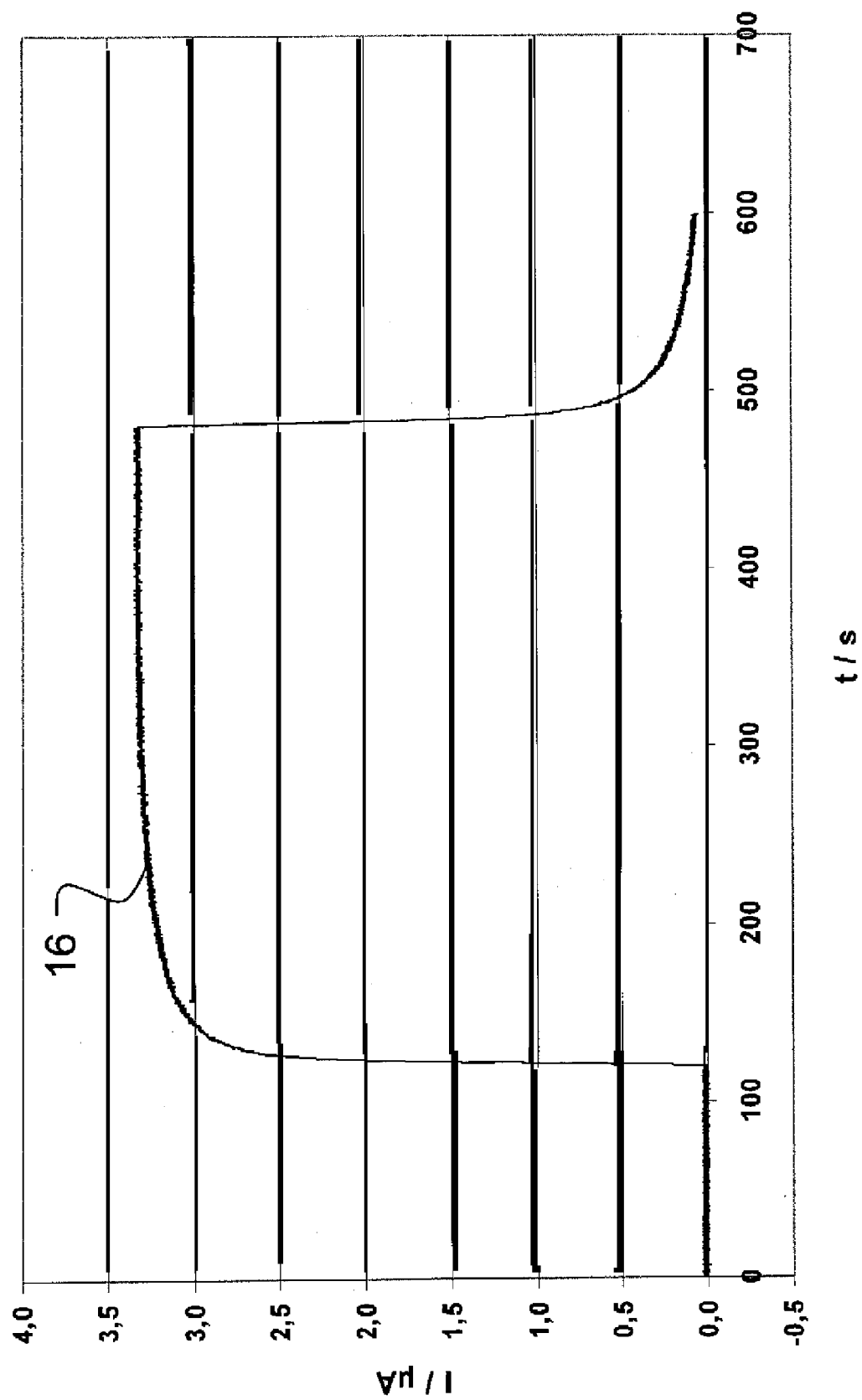
FIG. 2 is a gas admission curve.

FIG. 2 shows a typical gas admission curve 16 with the sensor 1 according to the present invention. Sensor 1 was exposed to a concentration of 1.96 ppm of $H_2S$ for 6 minutes at a temperature of 20° C. and 50% relative humidity. The gas admission time in seconds is plotted on the abscissa in FIG. 2 and the sensor current in microAmperes is plotted on the ordinate.

The following values are obtained as mean values from five sensors and five measurements:

$I_0$=7±2 nA (residual current)

$S$=3.0±0.1 µA ppm$^{-1}$ (sensor signal in µA per ppm of $H_2S$)

$D$=3.4±1.6% (drift)

$t_{0-90}$=41.8±18.6 sec (jump response up to 90% of the maximum sensor signal).

Sensor 1 according to the present invention is characterized by a very low residual current $I_0$ and by the broad measuring range, because both concentrations of a few ppm and gas concentrations in the percent range can be measured.

Figure 3:
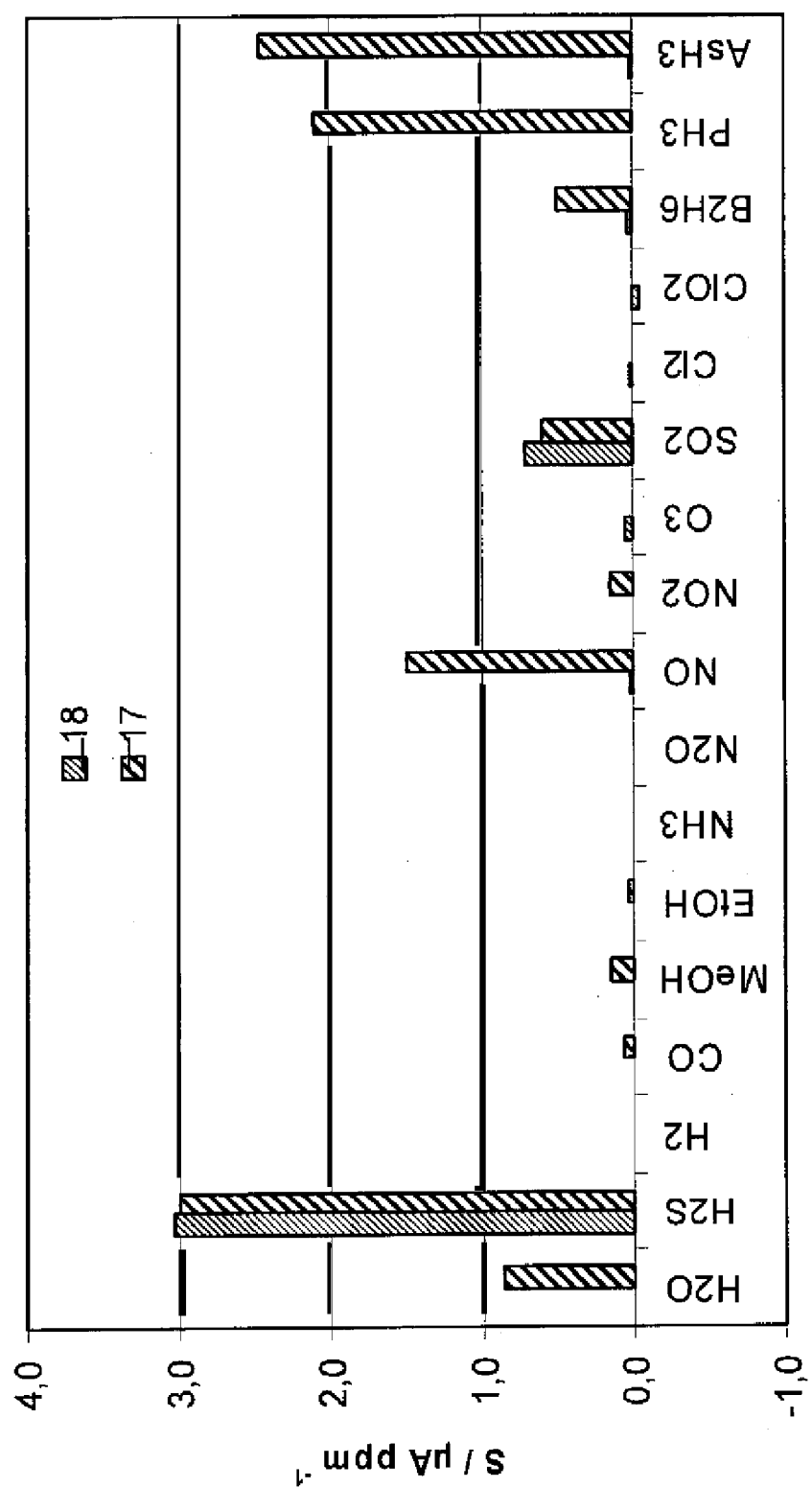
FIG. 3 is a graph showing a comparison of cross sensitivities.

FIG. 3 illustrates the cross sensitivities of a conventional electrochemical gas sensor with precious metal thick-layer electrode compared to the sensor 1 according to the present invention with the mediator compound. The darkly shaded bars 17 relate to the conventional gas sensor and the lightly shaded bars 18 to the sensor 1 according to the present invention. The tested gases are plotted on the abscissa in FIG. 3 and the sensor signal S in µA per ppm of $H_2S$ is plotted on the ordinate. As can be determined from FIG. 3, both sensors yield an approximately equal measured signal when $H_2S$ gas is admitted. However, the conventional gas sensor has marked cross sensitivities under the effect of moisture and in case of the gases $NO$, $PH_3$, $AsH_3$, $SO_2$ and $B_2H_6$. Sensor 1 according to the present invention has, by contrast, a cross sensitivity in case of $SO_2$ only. Since this is only one gas, this cross sensitivity can be compensated in a simple manner, for example, by a second sensor, which measures the $SO_2$ component only.

While specific embodiments of the invention have been shown and described in detail to illustrate the application of the principles of the invention, it will be understood that the invention may be embodied otherwise without departing from such principles.

What is claimed is:

1. An electrochemical gas sensor for detecting $H_2S$ in a gas sample, the electrochemical gas sensor comprising: a measuring electrode; another electrode; and an electrolyte solution containing a mediator compound in the form of metallates of transition metals, wherein a concentration of hydrogen sulfide in a gas is determined based on output from at least said measuring electrode, wherein a concentration of the metallates is in a range of 0.2 molar to 2.0 molar, and wherein said metallates comprise molybdates of a transition metal salt.

2. An electrochemical gas sensor in accordance with claim 1, wherein the measuring electrode consists of at least one of diamond-like carbon (DLC), boron-doped diamond (BDD), nitrogen-doped diamond and carbon nanotubes.

3. An electrochemical gas sensor in accordance with claim 1, wherein the measuring electrode comprises a precious metal thin-layer electrode with a layer thickness less than 600 µm.

4. An electrochemical gas sensor in accordance claim 1, further comprising:
   a sensor housing, said measuring electrode and said another electrode being arranged in said sensor housing, said electrolyte solution being in contact with said measuring electrode and said another electrode, wherein said metallates further comprise one or more of vanadates, chromates, tungstates and permanganates, said electrolyte solution comprising solid undissolved mediator compound solute in the form of said metallates of said transition metals.

5. An electrochemical gas sensor in accordance with claim 1, wherein a concentration of the metallates is about 1.0 molar.

6. An electrochemical gas sensor in accordance with claim 1, wherein the transition metal salt is a copper salt.

7. An electrochemical gas sensor in accordance with claim 1, wherein said copper salt is copper chloride and a concentration of the transition metal salt is in a range of 0.5 molar to 5.0 molar.

8. An electrochemical gas sensor in accordance with claim 1, wherein polybasic acids or their salts are added and a concentration of the transition metal salt is 3.0 molar.

9. An electrochemical gas sensor in accordance with claim 8, wherein citric acid, phthalic acid or citrates and phthalates are added as the polybasic acid.

10. An electrochemical gas sensor in accordance with claim 8, wherein boric acid or its alkali metal salts are used.

11. An electrochemical gas sensor in accordance claim 1, wherein inorganic salts or acid salts are added.

12. An electrochemical gas sensor in accordance with claim 1, wherein $NaHSO_4$ is added to the electrolyte solution, the electrolyte solution containing hygroscopic alkali or alkaline earth salts.

13. An electrochemical gas sensor in accordance with claim 1, wherein the electrolyte solution contains lithium chloride as a conducting salt.

14. An electrochemical gas sensor in accordance with claim 13, wherein a lithium chloride solution in the range of 2.0 molar to 10 molar is used.

15. An electrochemical gas sensor in accordance with claim 13, wherein a lithium chloride solution of about 3.0 molar is used.

16. An electrochemical gas sensor in accordance with claim 1, wherein the electrolyte solution contains water as a solvent.

17. An electrochemical gas sensor in accordance with claim 1, wherein the electrolyte solution contains one or more of organic solvents sulfolane, ethylene carbonate and propylene carbonate.

18. An electrochemical gas sensor in accordance with claim 1, wherein the electrolyte solution contains ionic liquids.

19. An electrochemical gas sensor, the electrochemical gas sensor comprising:
   a sensor housing;
   a measuring electrode in said sensor housing;
   another electrode in said sensor housing;
   an electrolyte solution in said sensor housing in contact with said measuring electrode and said another electrode, said electrolyte solution containing a mediator compound in the form of metallates of transition metals whereby the electrochemical gas sensor detects $H_2S$ in a gas sample, said metallates comprising molybdates of a transition metal salt, said electrolyte solution comprising solid undissolved mediator compound solute in the form of metallates of transition metals, wherein a concentration of the metallates is in a range of about 0.2 molar to 2.0 molar.

* * * * *